(12) United States Patent
Heerklotz et al.

(10) Patent No.: US 6,544,524 B2
(45) Date of Patent: Apr. 8, 2003

(54) ETHYL ACETATE EXTRACT FROM GUIGNARDIA USED TO TREAT AN INDIVIDUAL INFECTED BY FUNGI OR BACTERIA

(75) Inventors: Kátia Ferreira Rodrigues Heerklotz, Rio de Janeiro (BR); Jörg Arno Heerklotz, Rio de Janeiro (BR); Christa Werner, Rio de Janeiro (BR)

(73) Assignee: Fundacao Oswaldo Cruz - FIOCRUZ, Rio de Janeiro (BR)

( * ) Notice: Subject to any disclaimer, the term of this patent is extended or adjusted under 35 U.S.C. 154(b) by 0 days.

(21) Appl. No.: 09/918,717

(22) Filed: Aug. 1, 2001

(65) Prior Publication Data

US 2002/0048589 A1 Apr. 25, 2002

(51) Int. Cl.$^7$ .................. A61K 35/84; A01N 25/00; C12N 1/14; C12N 1/00
(52) U.S. Cl. .................. 424/195.15; 435/254.1; 435/911; 424/405
(58) Field of Search .................. 424/195.15, 780, 424/405; 514/449, 461; 435/254.1, 911

(56) References Cited

U.S. PATENT DOCUMENTS

| | | | | |
|---|---|---|---|---|
| 3,891,506 A | | 6/1975 | Munakata | .................. 195/80 R |
| 5,888,757 A | * | 3/1999 | Kuranda | |
| 5,919,746 A | | 7/1999 | Hirayama | .................. 510/392 |
| 6,303,302 B1 | * | 10/2001 | Rupp et al. | |

OTHER PUBLICATIONS

Hawley's Condensed Chemical Dictionary, 13th Edition, Revised by Lewis, 1997, p. 459.*

Gottlieb, OR; "Natural products research in Brazil"; Ciencia e Cultura. Journal of the Brazilian Association for the Advancement of Science; 49; (5,6); 315–320; 1997.

Baker, J.T. et al; "Natural product drug discovery and development: New perspectives on international collaboration"; Journal of Natural Products; 58 (9); 1325–1357; 1995.

Mothana, R.A.A. et al; "Ganomycins A and B, new antimicrobial farnesyl hydroquinones from the basidiomycete *Ganoderma pfeifferi*"; J. Nat. Product., 63; 416–418; 2000.

Afiyatullov et al; "New Diterpenic Atrosides of the fungus *Actemonium striatisporum* isolated from a Sea Cucumber"; J. Nat. Prod.; 63; 848–850; 2000.

Guo et al; "Cytonic Acids A and B; novel tridepside inhibitors of hCMV protease from Endophytic fungus *Cytonaema* species"; J. Nat. Product.; 63; 602–604; 2000.

Corthout, J. et al; "Antiviral ellagitannins from *S. mombim*"; Phytochemistry; 30; 1129–1130; 1991.

Stone, J. et al; "Endophytes of forest trees: a model for Fungus–Plant Interactions"; The Mycota V, Part B; Eds Carrol and Tudzynski Springer–Verlag, Berlin; pp 129–140; 1997.

Fungal endophytes of tree leaves; Microbial Ecology of leaves; Eds. Adrews, J. H.; Hirano, S.S. Springer Verlag, Berlin; 179–197; 1991.

* cited by examiner

*Primary Examiner*—Michael V. Meller
(74) *Attorney, Agent, or Firm*—Nixon & Vanderhye PC

(57) ABSTRACT

The present invention refers to extracts from the fungus Guignardia sp., and also a new isolate compound from the aforementioned extract, both having antimicrobial activities, particularly antibacterial and antifungal activities, and their use in pharmaceutical compositions. The new compound, isolated from the extract of the fungus Guignardia sp., presents a dioxolanone ring, having the following formula:

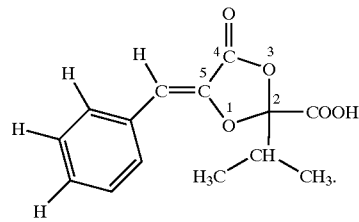

13 Claims, 2 Drawing Sheets

ETHYL ACETATE EXTRACT FROM GUIGNARDIA USED TO TREAT AN INDIVIDUAL INFECTED BY FUNGI OR BACTERIA

The present invention refers to extracts from the fungus Guignardia sp., and also a new isolate compound from the aforementioned extract, both having antimicrobial activities, particularly antibacterial and antifungal activities, and their use in pharmaceutical compositions.

The new compound, isolated from the extract of the fungus Guignardia sp., presents a dioxolanone ring, having the following formula:

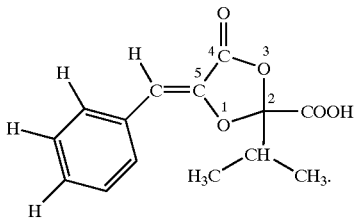

BACKGROUND OF THE INVENTION

The search for extracts obtained from plants, protista, fungi or animals and isolated molecules, identified and characterised from these extracts, having antimicrobial activities, has become one of the main motivators for the research and development of new drugs providing a larger scope of action and less toxicity. Furthermore, various pathogens that infect both animals and human beings are becoming resistant to many of the drugs presently in use which heightens the interest for new molecules.

After the major development of synthetic drugs that marked the second half of the 20th century, the nineties stand out as the era of research for drugs based on active principles obtained or isolated from natural products. The use of medicinal plants, protista, fungi and animals as raw material for isolating pure natural products, or for the obtainment of extracts and/or the formulation of phytotherapeutic products, consists an integral part of modern therapeutics.

The publications of natural products listed in Chemical Abstracts between 1985 and 1995 show that 21.1% were made by Japan, 10% by the US, another 10% by China, 8% by Germany, 8% by India, 4% by France and only 1.6% were contributed by Brazil (Gottlieb, O. R. "Natural products research in Brazil." Ciência e Cultura. Journal of the Brazilian Association for the Advancement of Science. 49. (5,6). 315–320. 1997).

Through the years, natural products have formed the basis for the treatment of illnesses of all the ancient cultures and continue to be the main source of primary health treatment for 80% of the world population. Sophisticated systems of traditional medicine have existed for thousands of years in many countries, such as China and India. Medicinal plants, protista, fungi and animals are also extensively used in the traditional systems of African medicine. Many phytodrugs are used in Europe and the US. Numerous examples of well known active principles derived from natural products can be cited, such as, for example, from plants: glycosides for the treatment of heart diseases obtained from *Digitalis purpurea* L.; the antihypertensive and tranquilliser reserpine, derived from the *Rauvolfia serpentine* (L.); quinine, antimalarial agent, from the Cinchona ssp.; the opiatic analgesics codeine and morphine from the *Papaver somniferum* L.; the antileucemic agents Vinblastine and Vincristine, from the *Catharanthus roseus* (L.) (see Baker, J. T., Borris, R. P., Carté, B., Cordell, G. A., Soejarto, D. D., Cragg, G. M., Gupta, M. P., Iwu, M. M., Madulid, D. R. and Tyler, V. E. "Natural product drug discovery and development: New perspectives on international collaboration". Journal of Natural Products. 58 (9), 1325–1357. 1995).

South America is becoming the focal point of much research in the field of natural products because it is considered one of the largest centres of biodiversity. South America is the continent of origin of many plants, Protista, fungi and animals that have already furnished—or demonstrate the potential to furnish—important products used in drugs.

As an example of the attempt to find natural molecules capable of acting against infectious agents, various efforts have been made, for example, to isolate and characterise at molecular level, a broad band of natural peptidic antimicrobial components obtained from animals (amphibians, frogs, mammals, insects), plants, fungi and bacterial species (Hanckoc et al., 1995). These biologically active peptides vary as to the scope of activity, mode of action, molecular weight (from 1.1 to more than 10 kDa), genetic origin and biochemical properties.

Various programs with the objective of identifying metabolites in extracts from fungi are also under way. *Ganoderma pfeifferi* Bres. (synonimous *Ganoderma cupreolaccatum* Kalchbr., *Ganoderma soniese* Steyaert) is a basidiomycete found only in Europe, and which lives on Fagus and various other trees such as Aesculus, Acer, Fraxinus, Prunus and Quercus. This species of basidiomycete is distinguishable from other older species such as *Ganoderma lucidum* and *Ganoderma resinaceum* by its dark brown context. *Ganoderma pfeifferi* is one of the lesser known species of the Ganodermaceteae family from the phytochemical investigation point of view. However, a reasonable number of triterpenes, polysaccharides and steroids, with interesting biological and pharmacological activities, have been isolated from the extracts of *G. lucidum* and *G. applanatum*.

Mothana et al (Mothana, R. A. A., Jansen, R., Jülich, W. and Lindequist, U. "Ganomycins A and B, new antimicrobial farnesyl hydroquinones from the basidiomycete *Ganoderma pfeifferi*. J. Nat. Prod., 63. 416–418. 2000) isolated and elucidated the structure of two hydroquinones obtained from the extract of the dichloromethane of *G. pfeifferi*. These compounds (i) acid 2-[2-(2.5 dihydroxyphenyl)-ethylidene]-11-hydroxy-6.10-dimythyl-undeca-5.9-dienic and (ii) acid acid 2-[2-(2.5 dihydroxyphenyl)-ethylidene]-6.10-dimythyl-undeca-5.9-dienic present antibacterial activity.

Marine fungi have also been cited as potential sources of active secondary metabolites of biological and chemical interest for the development of new pharmaceutical compositions. Afiyatullov et al (Afiyatullov, S. S., Kuznetsova, T. A., Isakov, V. V., Pivkin, M. V., Prokofeva, N. G., Elyakov, G. B. "New Diterpenic Atrosides of the fungus *Acremonium striatisporum* isolated from a Sea Cucumber. J.Nat. Prod. 63.848.–850.2000)] investigated the fungus *Acremonium striatisporum* isolated from the sea cucumber *Eupentacta fraudatrix*. The authors isolated and characterised two new diterpenic glycosides from this fungus (named virescinosides M and N) also isolating, furthermore, three known compounds (virescinosides A, B and C). These compounds presented cytotoxic effects on the eggs of the *Strongylocen-*

*trotus intermedius* during initial stages of development ($MIC_{50}$=2.7–20 μM) and also demonstrated cytotoxic activity, in vitro, against tumorous cells of Ehrlich's carcinoma (IC50=10–100 μM).

Furthermore, various other examples can be cited concerning the obtainment of extracts resulting from the fermentation of fungi and/or molecules obtained from these when showing interesting biological activity, amongst others, against human cytomegalovirus (Guo, B., Dai, J. R., Ng, S., Huang, Y., Leong, C., Ong, W. e Carté, B. "Cytonic Acids A and B: novel tridepside inhibitors of hCMV protease from Endophytic fungus Cytonaema species. J. Nat. Prod. 63.602–604-2000).

The U.S. Pat. No. 3,891,506 describes a substance, named quintomycin, with potential use as an antibiotic which is produced by the fungus *Streptomyces lividus*.

Concerning the fungus belonging to the genus Guignardia, it is possible to cite the obtainment of alkaline lipolitic enzymes isolated from this micro-organism, in particular from *G. laricina* and *G. paulowniae,* and its uses in detergents (see U.S. Pat. No. 5,919,746).

Despite being quite vast, medical knowledge still remains incomplete as to the fight against pathogenic micro-organisms having already infected the human organism, especially those originating from (i) nosocomial infections where the aerobiological micro-organisms constitute, for example, an important vector, (ii) food poisoning and (iii) the contamination of water. Furthermore, such micro-organisms may also become resistant to any known drug, even the latest generation ones, due to their possible biological mutations.

In this context, the development of new, more efficient drugs for the treatment of infections caused by these micro-organisms becomes urgent, especially bacteria and fungi, with the capability of having effect in cases where many strains have already become resistant to the drugs commonly employed and commercially available. In this sense, the search for natural extracts obtained from animals (amphibians, frogs, mammals, insects), plants, fungi and bacteria species has shown to be an interesting alternative to attend to the demand for more efficient drugs with lower toxicity to treat patients with generalised infections, caused by infection through fungi and bacteria, and which are common, for example, in hospital environments.

SUMMARY OF THE INVENTION

One of the purposes of the present invention is to provide extracts obtained from the fermentation of the fungus Guignardia sp.

Another purpose of the present invention is to provide, from the aforementioned extract of the fungus Guignardia sp., a new molecule containing a dioxolanone ring, or a salt of the same, having the following formula:

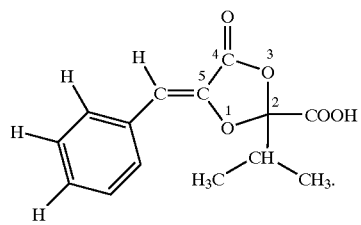

A first embodiment of the following invention relates to a pharmaceutical composition including the extract resulting from the fermentation of the fungus Guignardia sp. combined with a pharmaceutically acceptable vehicle.

A second embodiment of the present invention refers to a pharmaceutical composition including the molecule (Z)-5-benzylidene-2-isopropyl-4-oxo-1.3-dioxolane-2-carboxyl acid or a salt of the same combined with a pharmaceutically acceptable vehicle.

BRIEF DESCRIPTION OF THE DIAGRAMS

DETAILED DESCRIPTION OF THE INVENTION

Figure 1:
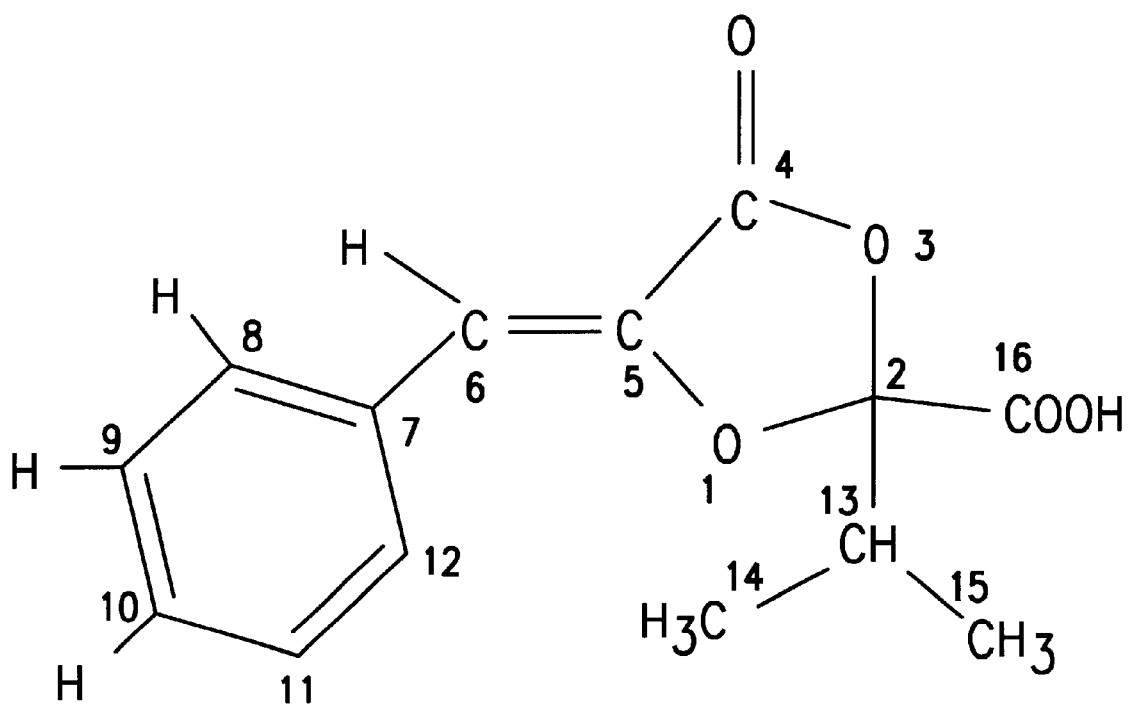
FIG. 1 represents the structure of the new compound of the invention (Z)-5-benzylidene-2-isopropyl-4-oxo-1.3-dioxolane-2-carboxyl acid and its numbering in accordance with the data of Table 1.

The Extract of the Fungus GUIGNARDIA SP.

The search for endophytic fungi in plants normally employed in traditional medicine has resulted in various studies. In the case of the present invention the facultative tree *Spondias mombin* L. (Anacardiaceae), common name Yellow Mombin (or Hog Plum), with a height varying between 20 and 25 meters is a species normally encountered in neotropical regions and with great diversity in the northern Amazonia and the Brazilian Atlantic forest. It became an important tree in an economic aspect, principally in Amazonia and northeastern Brazil, due to its edible fruit. Furthermore, the recent isolation of compounds with medicinal properties from the leaves of *S. mombin* has contributed to the increase of research concerning the chemical composition of its natural products (Corthout, J., Pieters, L., Claeys, M., Vanden Berghe, D. A. e Vlietinck, A. J. "Antiviral ellagitannins from *S. mombim*"— Phytochemistry.30. 1129–1130. 1991).

The diversity of the rate of endophytes detected from the plants that grow in tropical regions along with their potential role and the use of these fungi have been discussed by various authors. Much of the research concerning endophytic fungi has shown that a series of biotic and abiotic factors may influence the composition of the groups of fungus (Stone, J. and Petrini, O. Endophytes of forest trees: a model for Fungus-Plant Interactions. pp.129–140. In: The Mycota V, Part B. Eds. Carroll and Tudzynski. Springer-Verlag, Berlin. 1997). For example, it has been demonstrated that a fungus shows a preference for colonising determined plant tissues, also that normally isolated rates have shown in a consistent manner differences of frequency between organs. Petrini (Fungal endophytes of tree leaves. pp. 179–197. In: Microbial Ecology of leaves. Eds. Andrews, J. H., Hirano, S. S. Springer Verlag. 1991) has discussed the tissue and organ specificity shown by endophytic fungi as a result of the adaptation to the different physiological conditions of the plant.

The fungus Guignardia (Ascomycota) whose extracts are to be the object of the present invention was obtained as endophyte from the aerial part of the trees of the genus Spondias (Anacardiaceae) or closely related genera. The aerial parts are sterilised employing adequate alcoholic solvents including, but not limited to methanol, ethanol, 1-propenol, 2-propenol, iso-butanol, sec-butanol, posterior addition of a chlorine based agent, for example sodium hypochlorite, peracetic acid, $HgCl_2$, amongst others to the knowledge of those versed in the matter, and a wash with one of the aforementioned solvents. The aerial parts in the forms of disks were placed in Petri dishes with an agar medium, containing sources of carbon and nitrogen to the knowledge of those versed in the matter, supplemented with an antibiotic such as, for example, streptomycin or chloramphenicol, amongst others and incubated at ambient temperature. Each colony was then isolated and identified.

Once the fungus isolated, the extract of the same is obtained after fermentation, through the following sequences:

(a) Flasks containing an appropriate volume of medium containing sources of carbon and nitrogen, such as starch, glucose, glycerol, maltose, fructose, dextrine, galactose, peptone, meat extracts, ammonia salts, inorganic nitrate amongst others to the knowledge of those versed in the matter, are inoculated in aseptic conditions.

(b) The cultures are then incubated at ambient temperature and placed in a rotative agitator at approximately 110 rotations per minute (rpm).

(c) After fermentation, for an appropriate period of time, employing conditions to the knowledge of those versed in the matter the filtrate is then extracted with an organic solvent which, in this case may include, but is not limited to hexane, cyclohexane, ethyl acetate, dichloromethane, methanol or ethanol.

(d) The concentrated organic raw extracts may be obtained by evaporation under vacuum until dry. Dehydration is recommended in the case an aqueous raw extract is required, for example, through lyophilisation or dry aspersion.

As demonstrated previously the extracts of the present invention can be obtained by known processes.

The raw extracts may be used directly in the pharmaceutical formulations of the present invention or, alternatively, may be purified by appropriate methods as previously mentioned, such as, for example, fractionation by column chromatography, obtaining fractions with biological activity.

The Obtainment of the New Compound

Once the extracts obtained, in accordance with the sequences described above, the obtainment of the new compound of the present invention (Z)-5-benzylidene-2-isopropyl-4-oxo-1.3-dioxolane-2-carboxyl acid or, simply, guignardic acid can be undertaken through the purification of the extract, obtained in (d) above, with appropriate techniques such as, for example, thin layer chromatography and high resolution liquid chromatography.

The Pharmaceutical Compositions

The pharmaceutical compositions containing the raw extracts of Guignardia of the present invention, and also the new compound, can be administered through the digestive tract (orally or through the use of suppositories), or by parenteral or cutaneous means. The vehicles employed are known to those versed in the techniques.

For oral administration, the drug may be in the form of tablets, pills, capsules or in the form of solutions or suspensions. The solid compositions contain the active ingredient mixed with non-toxic excipients appropriate for the manufacture of tablets, such as starch, milk derived sugars, certain types of carbonates and/or bicarbonates, phosphates etc. The tablets may be coated or not, depending on the location where the disintegration and absorption of the drug should occur in the gastrointestinal tract. In the cases of aqueous suspensions or solutions, excipients such as methyl cellulose, sodium alginate, gum arabic, lecithin etc. may be used with one or more additives, such as preservatives, colourants, flavours, thickeners, etc.

The quantity of the extract to be combined with the pharmaceutically acceptable vehicle in a manner as to produce the appropriate form of dose will depend on the organism to be treated and the method of administration selected. However, in the case of the present invention the pharmaceutical compositions may contain, preferentially, the extract of Guignardia in a quantity varying from 1 to 50% in weight, for use in the treatment of infections caused by filamentous fungi, yeasts, bacteria and actinomycetes.

The quantity of the compound (Z)-5-benzylidene-2-isopropyl-4-oxo-1.3-dioxolane-2-carboxyl acid or its salt to be combined with the pharmaceutically acceptable vehicle in a manner as to produce the appropriate form of dose will depend on the organism to be treated and the method of administration selected. However, in the case of the present invention the pharmaceutical compositions may contain, preferentially, the aforementioned compound or its salt in a quantity varying from 1 to 50% in weight, for use in the treatment of infections caused by fungi or bacteria.

It must be understood that the specific level of the dose for any given patient will depend on a variety of factors including the activity of the specific compound employed, age, body weight, overall clinical condition, sex, diet, time and method of administration, rate of excretion, combination with other drugs and the severity of the illness to be treated.

The present invention is described in detail through the examples presented below. It is necessary to point out that the invention is not limited to these examples but also includes variations and modifications within the scope of which it functions.

EXAMPLE 1

Isolating the Fungus

Guignardia sp. (Ascomycota) was isolated as an endophyte from the sterilised surface of the leaves of the tree *Spondias mombin* L. (Anacardiaceae) collected in Rio de Janeiro. The leaves were sterilised within 24 hours after collection through the immersion of these in ethanol at 75% during 1 minute, followed by the addition of sodium hypochlorite with analytic purity (0–12% of chlorine) during 5 minutes and then washed with ethanol at 75% for 0.5 minutes. Leaves in the form of disks with a diameter of approximately 3mm were mounted in groups of five on Petri dishes containing cornflour agar with dextrose (CMD, Difco) supplemented with 4 g/l of streptomycin sulphate. The plaques were incubated at 22° C. Each colony was isolated for later identification through the transfer of the mycelium to a medium of cornflour agar with dextrose and/or 2% extract of malt agar (Difco). Stock cultures of Guignardia sp. were maintained in inclined tubes containing cornflour agar medium (Difco) at a temperature of 4° C.

EXAMPLE 2

Conditions for Culture and Extraction

Erlenmeyer flasks (250 ml) containing 50 ml of malt extract broth(20 g/l of malt extract, 1 g/l of peptone and 20 g/l of glucose) per flask were inoculated under aseptic conditions. The cultures were incubated at ambient temperature and placed in a rotative agitator (110 rpm). After fermentation in malt extract for 14 days the filtrate is removed (pH=4.5) and undergoes an extraction with ethyl acetate and posterior evaporation, under vacuum, until dry, obtaining 57.6 mg of raw extract.

EXAMPLE 3

Retention Time Data and $\lambda_{MAX}$ of the Principal Peaks Detected in the Extracts of Giugnardia Sp.

These results were obtained by high resolution liquid chromatography using conditions that are to the knowledge of those versed in the matter.

| Taxon | Tissue of plant | Locality | Retention time (min) | Wavelength (nm) |
|---|---|---|---|---|
| Guignardia sp. | Leaf | Rio de Janeiro | 5.4 | 225 |
| | | | 8.3 | 225,275 |
| | | | 9,6 | 225sh,305, 320sh |
| | | | 10,6 | 225sh,305, 320sh |
| | | | 17,0 | 265 |

EXAMPLE 4
Biological Activity of the Guignardia Sp. Extract

The tests for the biological activity of the raw extract obtained in EXAMPLE 2 above were undertaken employing no more than routine methodology that is to the knowledge of those versed in the matter.

As a result of an initial scan of the raw extract of Guignardia sp. and using a test on calibration plaques strong inhibition was verified on the following micro-organisms: Actino sp. (Gram positive filamentous bacteria), *Escherichia coli* (Gram negative bacteria), *Staphylococcus aureus* (Gram positive bacteria), *Saccharomyces cerevisae* (yeast), Geotrichum sp. (filamentous fungus), *Penecillium canadensis* (filamentous fungus).

TABLE 1

Biological activity demonstrated by the raw extract of Guignardia sp.

| | Actinomycete | bacteria | | Yeast | fungus Filamentous | |
|---|---|---|---|---|---|---|
| Taxon | ACT | ESC | STA | SAC | GEO | PCA |
| Guignardia sp. | 1 | 1 | 1 | 1 | 1 | 1 |

Key: 0 - no inhibition; 1 - inhibition
ACT: Actino. Sp.
Gram positive and Gram negative bacteria - ESC: *E. coli*; STA: *S. aureus*
Yeast - SAC: *S. cerevisae*
Filamentous fungi - GEO: Geotrichum sp., PCA: *P. canadensis*

EXAMPLE 5
Isolation of the Compound

The purification was undertaken by the separation of the extract employing fine layer chromatography (silica gel, $CHCl_3$:MeOH:$NH_4OH$(25%), in the following proportions 78:19:3, respectively). Eight active bands in ultraviolet were generated from the plaques and eluated with MeOH:$CHCl_3$ in the proportion of 8:2, respectively. The guignardic acid compound was isolated from the fraction 2 ($R_f$: 0.2) that presented elevated bioactivity by a semipreparative high resolution liquid chromatography: column $C_8$ nucleosil (7 μm, 10×250 mm; Macherey-Nagel, Oensingen, Switzerland); flow rate of 5 ml min$^{-1}$, solvent system: A=$H_2O$ and B=MeOH with a linear gradient varying from 100% of the solvent A to 100% of the solvent B in 20 minutes, followed by passing the solvent B at 100% for 5 minutes. Through this procedure it is possible to obtain 12 mg of the guignardic acid compound.

EXAMPLE 6
Characterisation of Guignardic Acid

The official name of the compound according to the IUPAC nomenclature is (Z) -5-benzylidene-2-isopropyl-4-oxo-1.3-dioxolane-2-carboxyl acid and its structure is shown in FIG. 1. The elucidation of its structure was done using a combination of the methods of Nuclear Magnetic Resonance (NMR) in 1D and 2D [$^1$H, $^{13}$C Distortionless Enhancement by Polarisation Transfer—DEPT, $^1$H, $^{13}$C COSY (Correlated Spectroscopy), HMQC (a modern inverse version of experiment C, H—COSY that shows the correlations $^1$J—C, H) and HMBC (Heternuclear Multiple Bonding Correlation)], ultraviolet, infrared, mass spectroscopy and CD Spectrum (circular dichroism).

Not only the NMR spectrum of the $^{13}$C and the DEPT, but also the HMQC and HMBC experiments in dimethyl sulphoxide ($d^6$-DMSO)allowed the detection of 14 carbon atoms, including two carbonyls ($\delta_c$ 166.5 and 164.6), an olefinic methyne ($\delta_c$ 104.0/$\delta_H$ 6.22), two carbon quaternaries (one olefinic in $\delta_c$ 139.1 and one in $\delta_c$ 111.1, that indicate the presence of an acetal group, as well as a methyne ($\delta_c$ 31.5/$\delta_H$ 2.62)and two methyl groups ($\delta_c$ 16.4/$\delta_c$ 15.1). Typical signs of a monosubstituted phenyl ring are also encountered in the NMR spectrum of the $^{13}$C.

The NMR spectrum of $^1$H presented a doublet in $\delta_H$ 7.66 (2H) and two triplets in $\delta_H$ 7.38 (2H) and $\delta_H$ 7.27 (1H)also attributed to the monosubstituted phenyl ring. A simplex in $\delta_H$ (1H) shows an olefinic proton. The signal in $\delta_H$ 2.62 shows a septet which jointly with two doublets in $\delta_H$ 0.92 and $\delta_H$ 0.95, identify an isopropyl group (data from the NMR spectrum of the $^{13}$C and the $^1$H compound of the present invention are detailed in Table 2 in consonance with FIG. 1).

TABLE 2

Data from the NMR spectrum of the $^{13}$C and the $^1$H in consonance with the numbering shown in FIG. 1).

| C/H | $\delta_c$ ppm | $\delta_H$ ppm |
|---|---|---|
| 16 | 166.5 (s) | — |
| 4 | 164.6 (s) | — |
| 5 | 139.1 (s) | — |
| 2 | 111.0 (s) | — |
| 7 | 133.3 (s) | — |
| 8+12 | 129.1 (d) | 7.66(2H, t, J = 7.4 Hz) |
| 9+11 | 128.8 (d) | 7.38(2H, t, J = 7.7 Hz) |
| 10 | 128.1 (d) | 7.27(1H, t, J = 7.4 Hz) |
| 6 | 104.0 (d) | 6.22 (1H, s) |
| 13 | 31.6 (d) | 2.62(1H, sept., J = 6.8 Hz) |
| 14 | 15.1 (q) | 0.92(3H, d., J = 6.9 Hz) |
| 15 | 16.4 (q) | 0.95(3H, d., J = 6.9 Hz) |

Two carbonyls and four double bonds are responsible for presence of 6 saturations. Two remaining levels of saturation suggest that the compound possesses two rings, with one of them being the monosubstituted phenyl ring.

Guignardic acid (GA) from the data of the electrospray of the mass spectroscopy presented the molecular weight of 262 m/z undertaken in a Finnigan TSQ 700 spectrometer equipped with an atmospheric pressure chemical ionisation source (APCI). The molecular weight of guignardic acid was obtained through ES-MS in negative mode. ES-MS showed the molecular ion as [M–H]$^-$ at m/z 261 which indicates the molecular weight at 262, indicating thus, an identical number or absence of nitrogen. The mass spectrum in tandem (MS/MS)of the parental ion in 261 m/z presented two significant products: (i)one in 217 m/z, which was originated by the loss of a carboxyl group such as $CO^2$ and (ii)another in 189 m/z, which is the principal fragmentation ion and can be described as [M—H—$CO^2$—CO]$^-$.

The molecular formula $C^{14}H^{14}O^5$ was deduced from the number of protons and atoms of carbon found in the NMR spectrum of $^1$H and $^{13}$C, combined with the mass spectrum.

The ultraviolet spectrum in MeOH of the compound of the invention showed an absorption at $\lambda_{max}$ in 301 and 225 sh nm, suggesting a chromophore system and which provides evidence that the double exocyclic bond is configured as (Z) (Hans-Joachim Brunk et al. Chem. Ber.116. 2165–2172. 1983; Ramage, R. et al. J. Chem. Soc. Perkin Trans. I.1531.1984).

The infrared spectrum was measured in a Perkin Elmer 297 type spectrometer and presented the following data in cm: $v_{max}$ (CHCl3) 3404br, 3109w, 3068w, 2992m, 2962m, 2879w, 2837w, 1783s, 1666s, 1646w, 1495w, 1450w, 1400w 2360m, 1339w, 1320w, 1301w, 1273w, 1182w, 1167w, 1152w, 1094m, 1059w, 1009m, 974w, 958w, 917w, 881w, 862w, 823w.

The ample vibration starting with OH at 3404 $cm^{-1}$, together with a strong absorption of C=O at 1666 $cm^{-1}$ shows evidence of an acid group. Lactones composed by a 5 member ring at 1783 $cm^{-1}$ appear as a result of the absorption of a C=O group. Two C=C conjugated with an aromatic ring and with C=O at 1646 $cm^{-1}$ were also detected.

Figure 2:
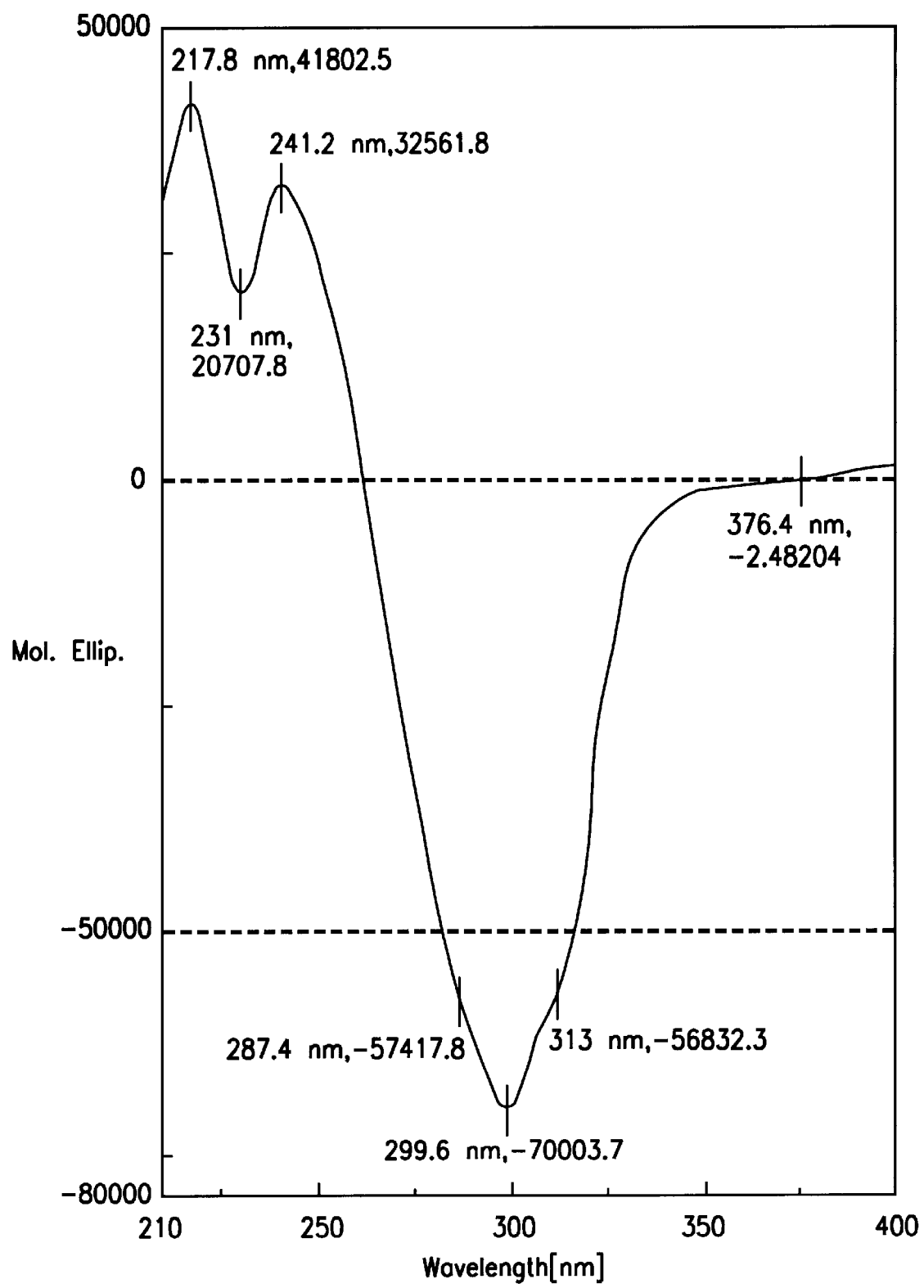
FIG. 2 shows the spectrum of circular Dichroism (CD)

The value of the optical rotation of guignardic acid is $[\alpha]^{20}D=56.5$ (c 0.2 EtOAc) showing that this compound is quiral. The exact quirality in the quiral centre is not known at the present moment, however there is confirmation through the optical rotation and from the CD spectrum demonstrated in FIG. 2.

EXAMPLE 7

Biological Activity of the Compound (Z)-5-benzylidene-2-isopropyl-4-oxo-1.3-dioxolane-2-carboxyl acid (GUIGNARDIC ACID).

Guided fractionation of the bioactivity of the extract of ethyl acetate (obtained in EXAMPLE 2 above)resulted in the isolation of the new optically active guignardic acid compound. The antimicrobial activity of this compound was detected employing the bioautographical method on a layer of agar (Rahalison,L.; Hamburger, M., Hostettmann, K.; Monod, M.; Frenk, E. Phytochemical Ananlysis.2.199–203.1991). The following microorganisms were tested: *Escherichia coli* (ATCC 25922) and *Staphylococcus aureus* (ATCC 25923). The medium used was the Mueller-Hinton in agar (Oxoid). The cultures grew during the night in nutrient medium broth number 3 (Fluka). For the bioautographic test the cultures were standardised through successive dilutions in $10^5$ cells/ml. The plaques were incubated at 37° C. for a period of 24 hours, sprayed with an aqueous solution of Methylthiazolyltetrazolium chloride (MTT)at 0.25% and then incubated for a further two hours at 37° C. The active fractions were detected under the form of white areas of inhibition on a lilac background.

The antibacterial activity verified for the compound of the invention was of $1.5 \times 10^{-7}$ molar against *E. coli* and $0.75 \times 10^{-7}$ molar against *S. aureus*.

What is claimed is:

1. A composition comprising an ethyl acetate extract from a filtrate of Guignardia, said composition having antimicrobial activity.

2. The composition of claim 1 wherein said composition is lyophilized.

3. The composition of claim 1 or claim 2, further comprising a pharmaceutically acceptable carrier.

4. A method of treating an individual infected by at least one of a fungi or bacteria comprising administering the composition of claim 1 or claim 2 to said individual.

5. The method of claim 4 wherein said individual is infected by at least one of a filamentous fungi, yeasts, actinomicetes or bacteria.

6. The method of claim 5 wherein said individual is infected by a Gram negative bacteria.

7. The method of claim 6 wherein said individual is infected by *Escherichia coli*.

8. The method of claim 5 wherein said individual is infected by a Gram positive bacteria.

9. The method of claim 8 wherein said individual is infected by a *Staphylococcus aureous*.

10. The method of claim 5 wherein said individual is infected by a filamentous fungi.

11. The method of claim 10 wherein said individual is infected by at least one of a Geotrichum sp. or *Penicillium canadensis*.

12. The method of claim 5 wherein said individual is infected by an actinomicetes.

13. The method of claim 12 wherein said individual is infected by Actyno sp.

* * * * *